(12) United States Patent
Schmieding

(10) Patent No.: US 6,270,503 B1
(45) Date of Patent: Aug. 7, 2001

(54) SYSTEM FOR OSTECHONDRAL FLAP REPAIR AND METHOD

(75) Inventor: Reinhold Schmieding, Naples, FL (US)

(73) Assignee: Arthrex, Inc., Naples, FL (US)

(*) Notice: Subject to any disclaimer, the term of this patent is extended or adjusted under 35 U.S.C. 154(b) by 0 days.

(21) Appl. No.: 09/497,111

(22) Filed: Feb. 3, 2000

Related U.S. Application Data (60) Provisional application No. 60/118,515, filed on Feb. 3, 1999.

(51) Int. Cl.[7] .................................................. A61B 17/58
(52) U.S. Cl. ........................................................ 606/88
(58) Field of Search ................... 606/80, 82, 86, 606/87, 88, 89, 96, 98, 99, 100, 104, 213, 220, 53, 60, 72, 79

(56) References Cited

U.S. PATENT DOCUMENTS

| | | | |
|---|---|---|---|
| 4,465,065 | * | 8/1984 | Gotfried .................. 606/96 |
| 4,744,353 | * | 5/1988 | MacFarland ............. 606/96 |
| 5,129,906 | * | 7/1992 | Ross et al. .............. 606/77 |
| 5,250,055 | * | 10/1993 | Moore et al. ........... 606/86 |
| 5,531,751 | * | 7/1996 | Schulthesis et al. .... 606/96 |
| 5,683,400 | * | 11/1997 | McGuire ................. 606/96 |
| 5,766,221 | * | 6/1998 | Benderev et al. ....... 606/96 |

\* cited by examiner

Primary Examiner—Jeffrey A. Smith
Assistant Examiner—Eduardo C. Robert
(74) Attorney, Agent, or Firm—Ostrolenk, Faber, Gerb & Soffen, LLP

(57) ABSTRACT

A method of fixation of osteochondritis dissecans fragments in which chondral fragments are approximated to bone using a guide sleeve having multiple parallel guide tunnels. A drill is inserted through one of the guide tunnels, and a hole is drilled through the fragment and into the bone to a predetermined depth. A fragment-retaining implant inserted into the hole secures the fragment to the bone. Further holes are drilled while the fragment is held in place with the guide sleeve. The implant is inserted using the guide sleeve as a guide.

7 Claims, 9 Drawing Sheets

SYSTEM FOR OSTECHONDRAL FLAP REPAIR AND METHOD

This application claims the benefit of U.S. Provisional Application Serial No. 60/118,515, filed Feb. 3, 1999, the entire disclosure of which is incorporated herein by reference.

BACKGROUND OF THE INVENTION

1. Field of the Invention

The present invention relates to a system for repairing a detached osteochondral flap. More specifically, the present invention relates to fixation of osteochondritis dissecans fragments using a parallel guide sleeve.

2. Description of the Related Art

Osteochondritis dissecans is a condition of complete or incomplete separation of a portion of joint cartilage and underlying bone. Usually involving the knee, the disorder also can affect the talar dome of the ankle and capitellum of the elbow. Reports of lesions in the shoulder, hands, wrist, and hip are rare. In the knee, the lesions are found most commonly on the medial femoral condyle, and less so on the lateral femoral condyle and the patella. On the medial femoral condyle, the lesions are most commonly found on the lateral, non-weight bearing surface.

Treatment usually involves osteochondral flap reattachment or abridement. Reattachment is preferred where possible, but the current methods of fixation using, e.g., a Kirschner wire, can be improved upon to simplify the technique and improve fixation strength.

SUMMARY OF THE INVENTION

The present invention provides a instrumentation for and a method of fixation of osteochondritis dissecans fragments using bioabsorbable chondral darts inserted through a clear guide sleeve. The instruments provide compression to an osteochondral fragment during insertion of the chondral darts below the surface of the articular cartilage. Dart insertion provides a strong, bioabsorbable fixation of smaller osteochondral flaps, particularly those of 5 mm to 20 mm in diameter. The present invention provides instrumentation that is designed for insertion of individual darts or, alternatively, multiple parallel dart insertion.

The single shot instruments of the present invention are designed to insert individual darts. The sheath is placed against the fragment to provide compression. A stainless steel trocar passes through the sheath to a controlled depth to form a hole. The chondral dart is inserted directly into the sheath and the sheath is positioned firmly over the drilled hole. The dart depth is controlled such that the dart is countersunk 2 mm below the surface of the cartilage into subchondral bone.

According to an alternative method of use and instrumentation, multishot instrumentation offers a controlled method to manage larger fragments using multiple darts. Clear guide sleeves, preferably having 2 or 4 parallel holes provide atraumatic compression to the fragment throughout the procedure while allowing the surgeon to see the passage of instruments and underlying fragment through the sheath. A set of drill pins having stepped lengths is used. The step design of the drill pins allows easy access for drilling and removing. These pins stabilize the guide sleeve to create necessary pilot holes for dart insertion. The dart is inserted through one of the channels into the subchondral bone 2 mm below the surface of the cartilage.

According to a preferred embodiment, darts are inserted by replacing drill pins in a last in, first out method. Thus, while holding the osteochondral flap fragment in place using the guide sleeve, a hole is drilled through the fragment and into the bone to a predetermined depth using the longest drill. The drill then is removed from the guide sleeve. A fragment-retaining dart implant is inserted into the hole to secure the fragment to the bone using the guide sleeve as a guide. The sequence then is repeated with the next longest drill, until all of the drills are removed. An auxiliary pin is used to hold the guide in place during the last installation sequence, which is performed using the shortest drill.

Other features and advantages of the present invention will become apparent from the following description of the invention which refers to the accompanying drawings.

DETAILED DESCRIPTION OF THE PREFERRED EMBODIMENTS

Referring initially to FIGS. 1–4, a single-shot guide sleeve 2 is shown. The guide sleeve has a proximal end 4 and a distal end 6, and two parallel guide tunnels 8 formed along its length. A larger diameter section provides a handle 9 for manipulation by the surgeon. Preferably, the guide sleeve is sufficiently transparent that instruments inserted into the tunnels can be visualized arthroscopically.

Referring to FIGS. 5–8, a multi-shot guide sleeve 10 is shown having five tunnels 12 extending from proximal end 14 to distal end 16.

The proximal ends 4, 14 of the guide sleeves are square for ease of manipulation. The circular distal ends 6, 16 preferably have a slight concave radius so as to conform to the chondral surface during surgical approximation of the fragment, as described more fully below.

Figure 1:
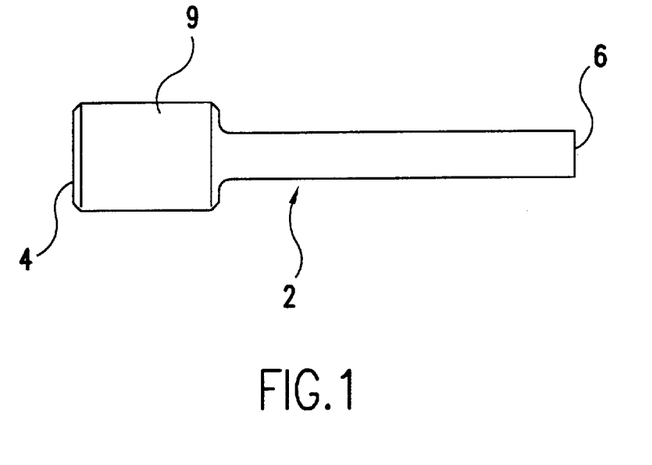
FIG. 1 is an elevation of a single-shot guide sleeve according to the present invention.
Figure 2:
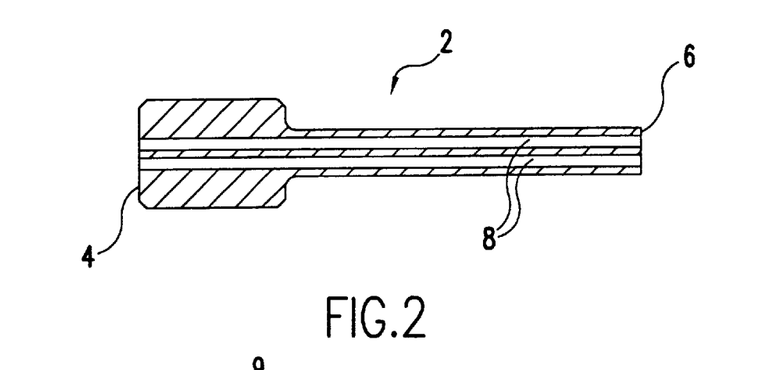
FIG. 2 is a plan section of the guide sleeve shown in FIG. 1.
Figure 3:
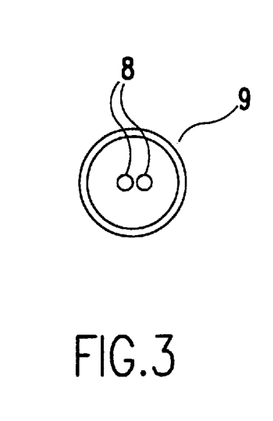
FIG. 3 is a proximal end view of the guide sleeve of FIG. 1.
Figure 4:
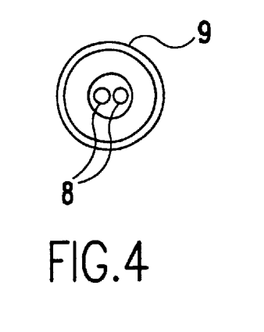
FIG. 4 is a distal end view of the guide sleeve of FIG. 1.
Figure 5:
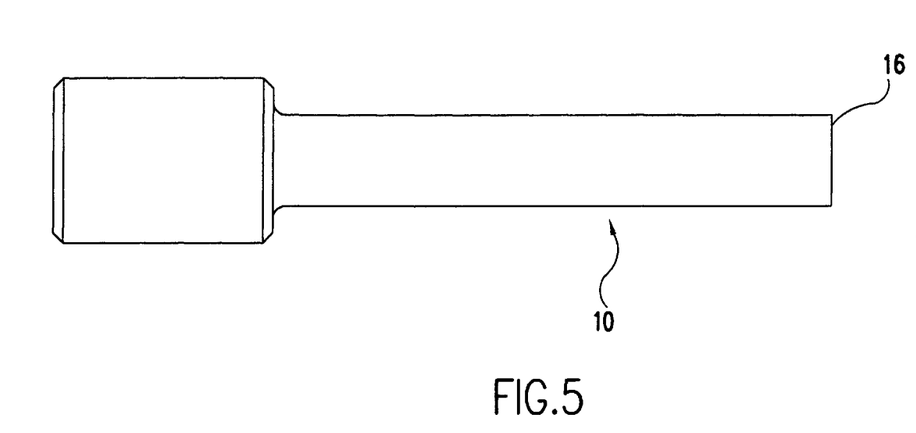
FIG. 5 is an elevation of a multi-shot guide sleeve according to the present invention.
Figure 6:
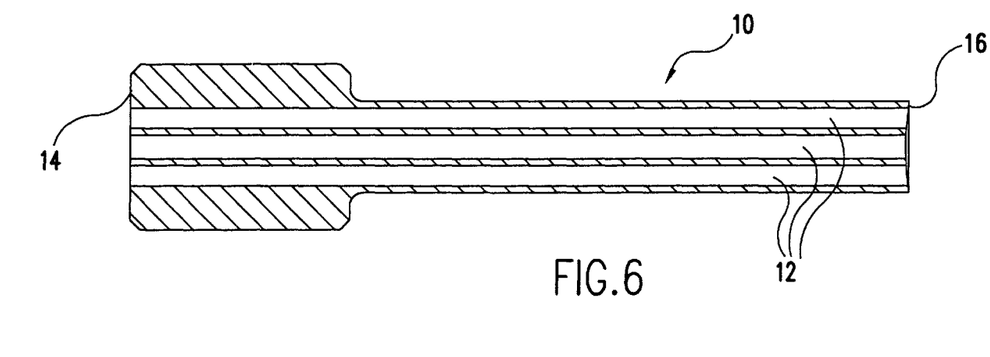
FIG. 6 is a plan section of the guide sleeve shown in FIG. 5.
Figure 7:
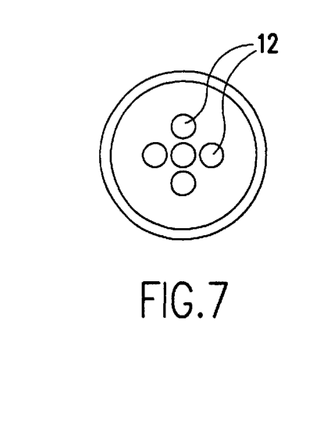
FIG. 7 is a proximal end view of the guide sleeve of FIG. 5.
Figure 8:
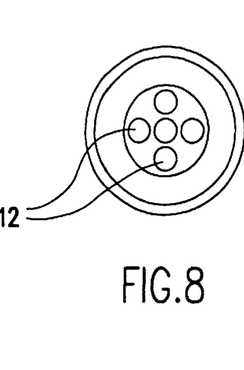
FIG. 8 is a distal end view of the guide sleeve of FIG. 5.
Figure 9:
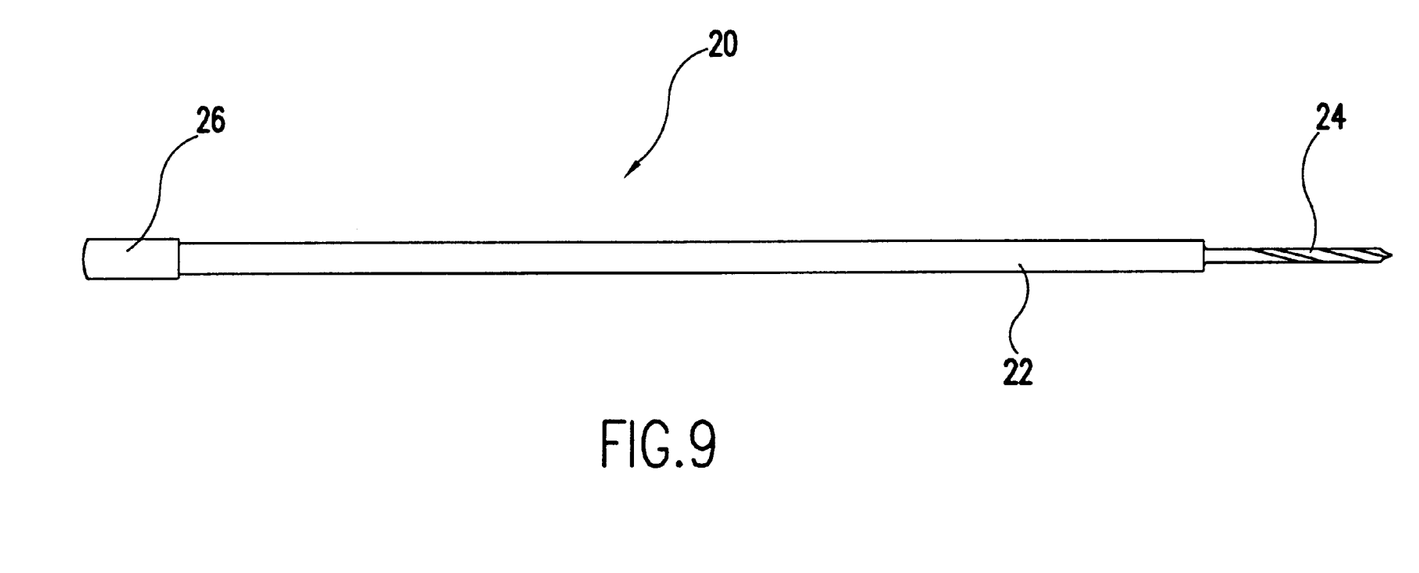
FIG. 9 illustrates generally a drill pin according to the present invention, the drill pin being provided in four sizes: short, medium, long, and extra long.

Referring to FIG. 9, a drill pin 20 according to the present invention is shown. The drill pin has a shaft 22 with a fluted distal end 24. A radius step between the distal end 24 and shaft 22 engages a guide sleeve surface to provide a depth stop, as described below. In a preferred embodiment for insertion of multiple fixation implants into a osteochondral flap, four drills are provided in stepped lengths. Accordingly, larger diameter proximal end 26 is, respectively, 0.333", 0.667", 1.000", and 1.333" in length for use in the preferred multi-shot procedure outlined below.

Figure 10:
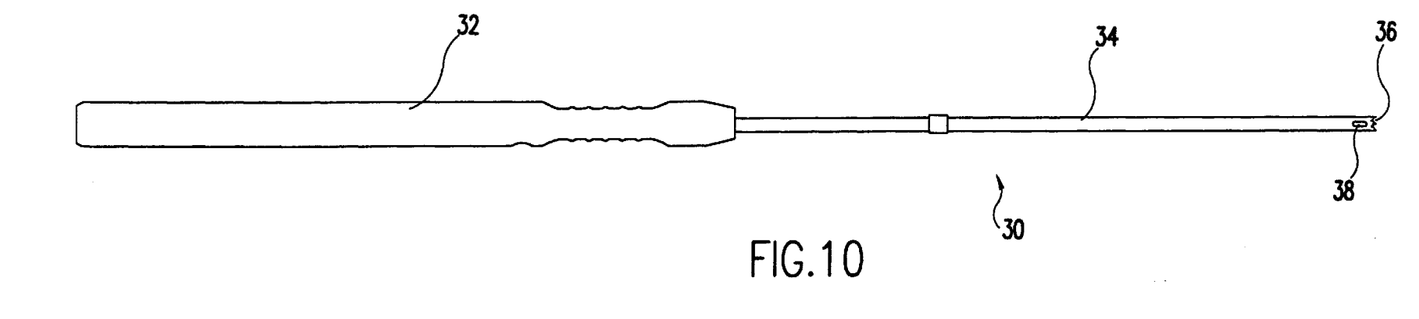
FIGS. 10–11 illustrate an osteochondral flap repair sheath according to the present invention.
Figure 11:
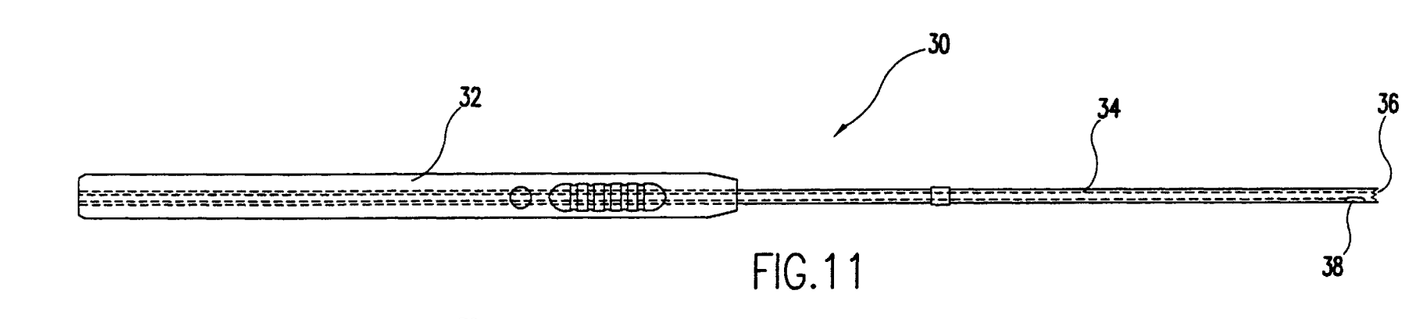

Referring to FIGS. 10–11, a repair sheath 30 according to the present invention is shown. Repair sheath 30 fits inside tunnels 8, 12 of guide sleeves 2, 10 and helps to stabilize the fracture. The sheath 30 has a cannulated handle 32 attached to a cannulated shaft 34. The distal end 36 of shaft 32 has serrated teeth to assist in stabilizing the osteochondral flap. A window 38 is provided for visualization through an arthroscope.

Figure 12:
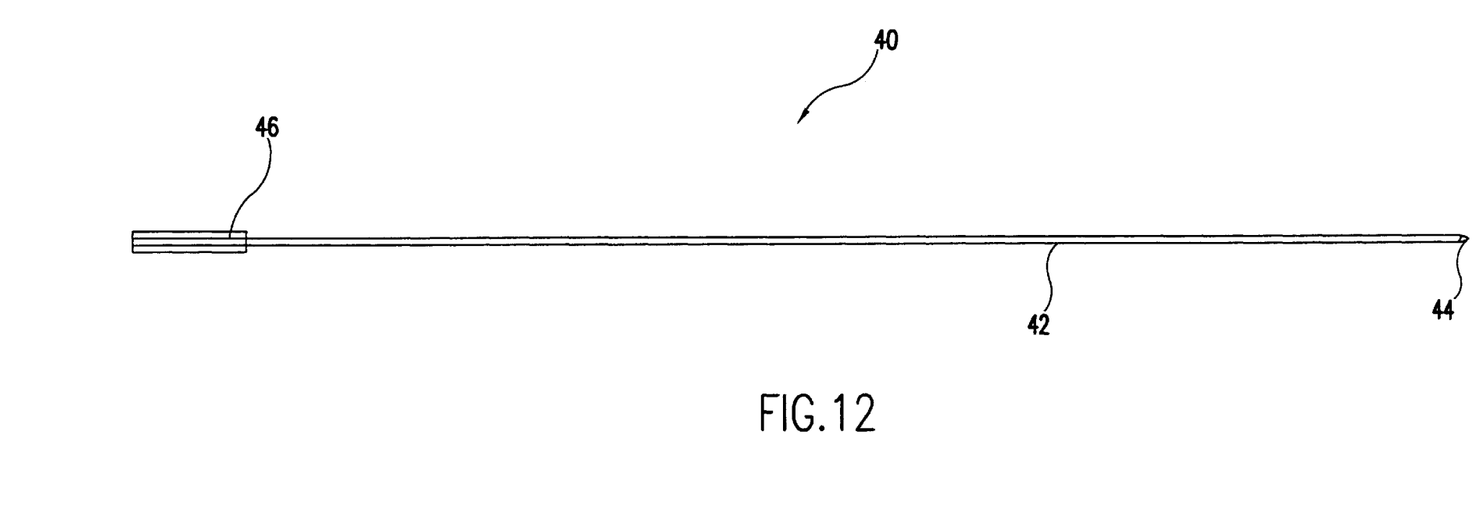
FIG. 12 illustrates an osteochondral flap repair trocar according to the present invention.

Referring to FIG. 12, a repair trocar 40 is shown which can be used to form the hole for receiving the fragment-retaining implant in place of drills 20, preferably in the single-shot method of the present invention described in more detail below. The trocar 40 has an elongate shaft 42 having a trocar tip 44 on the distal end, and a stepped radius resulting in a proximal end 46 having a larger diameter.

Figure 13:
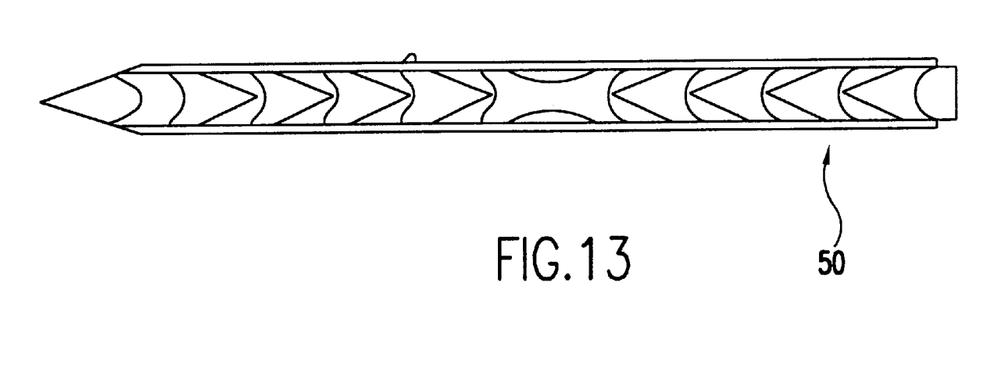
FIGS. 13–15 show an osteochondral flap repair dart according to the present invention.
Figure 14:
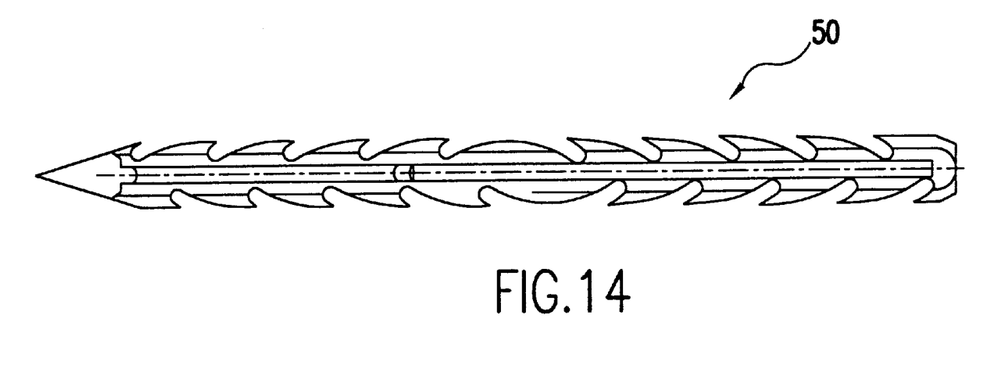
Figure 15:
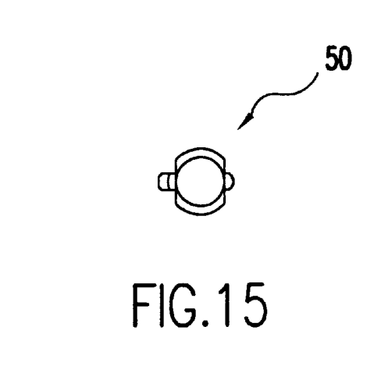

Referring to FIGS. 13–15, an 18 mm implant 50 according to the present invention is shown. The implant is similar to one originally designed for meniscal repair, and is described in allowed U.S. patent application Ser. No. 09/099,869, filed Jun. 19, 1998, the entire disclosure of which is incorporated herein by reference.

Figure 16:
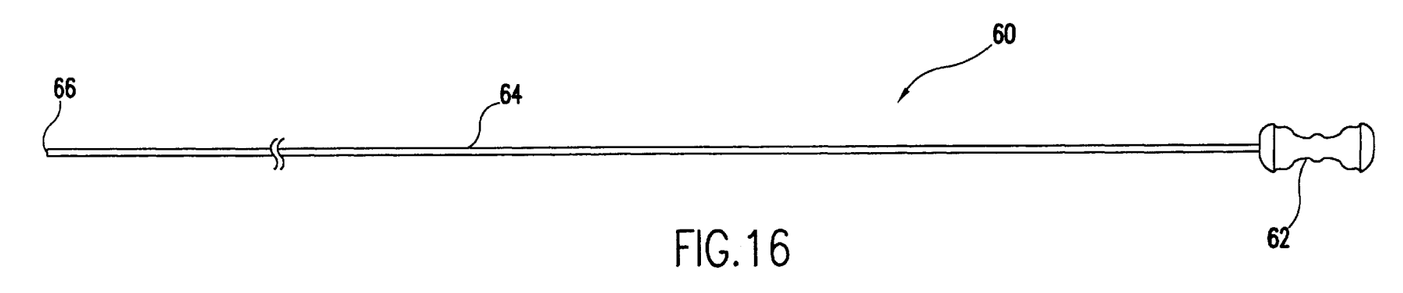
FIGS. 16–17 show an osteochondral flap repair dart inserter according to the present invention.
Figure 17:
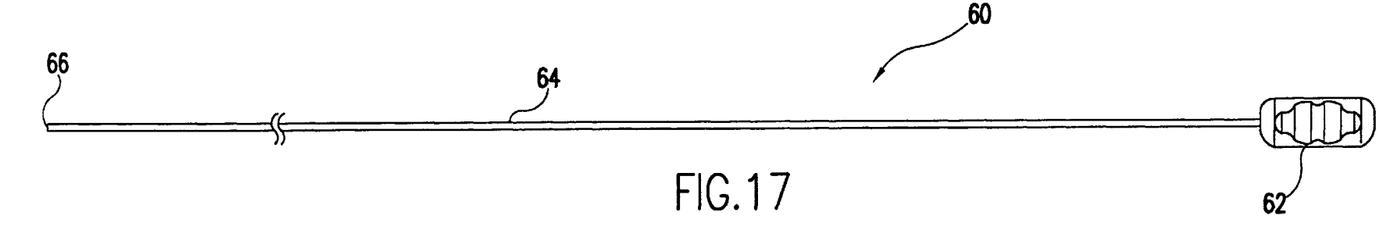

Referring to FIGS. 16 and 17, an implant inserter 60 according to the present invention is shown. Implant inserter 60 has a proximal handle 62 attached to an elongate shaft 64 which terminates in a flat end 66. The inserter is used to install the repair implant according to the preferred method outlined below.

Figure 18:
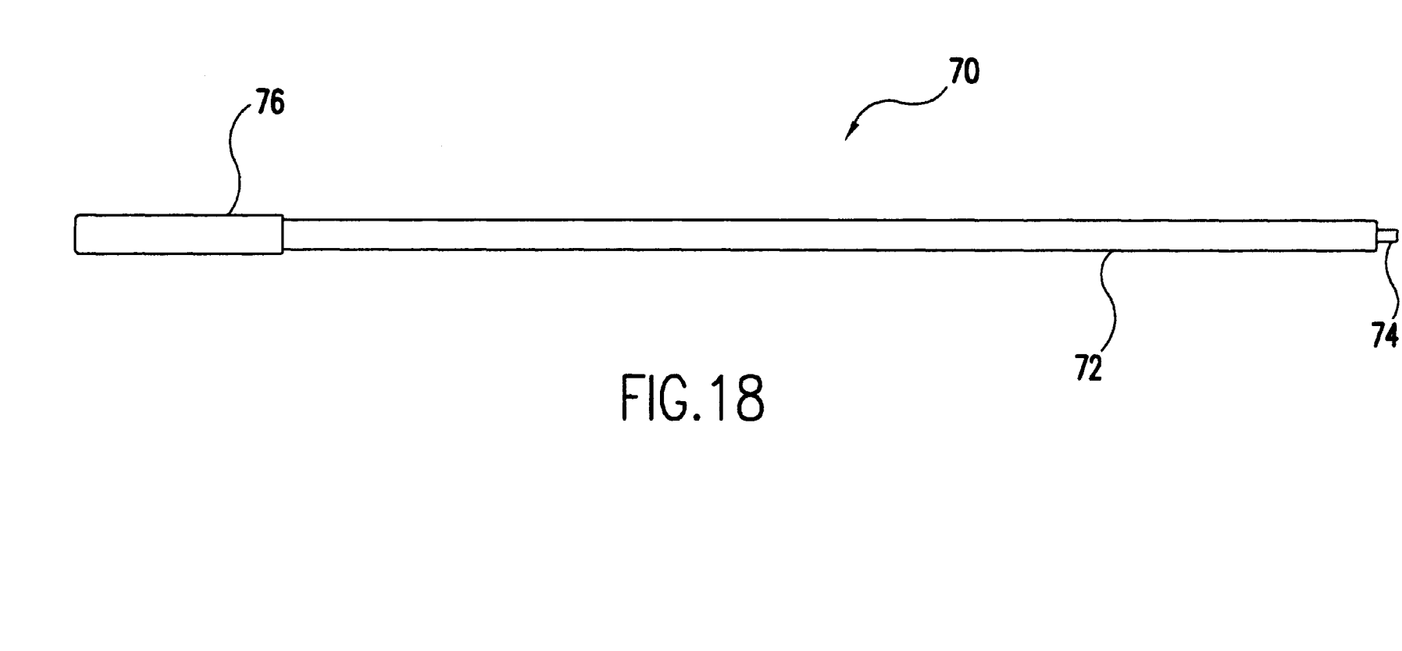
FIG. 18 shows an osteochondral flap repair blunt pin according to the present invention.

Referring to FIG. 18, a blunt pin 70 is shown. Blunt pin 70 has a shaft 72 provided on a distal end with a short pin 74. A stepped radius toward the proximal end 76 acts as a depth stop.

Figures 19, 20:
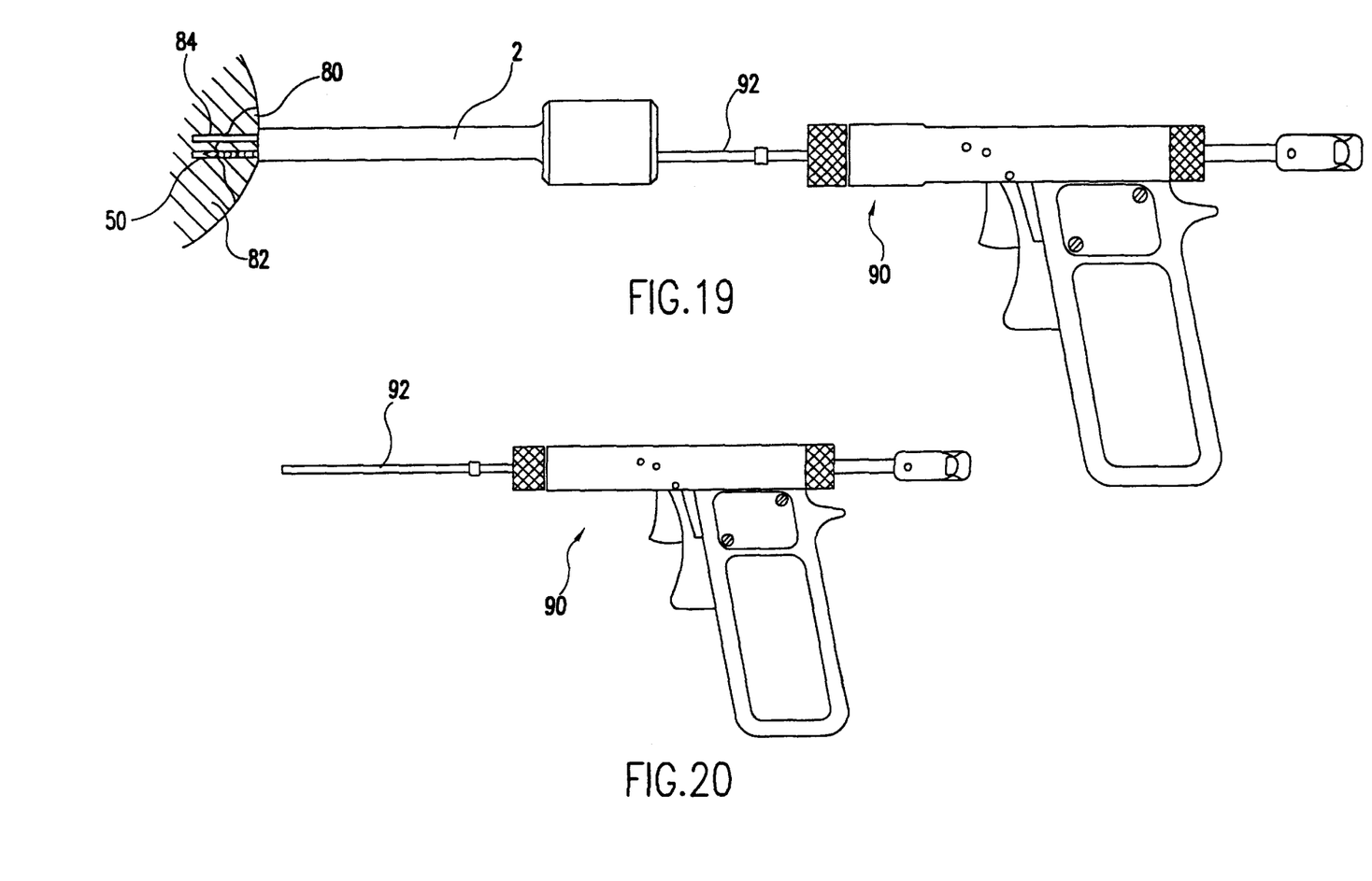
FIG. 19 is a schematic illustration of a method of repairing a detached osteochondral flap according to the present invention.
FIG. 20 illustrates an automatic implant gun for installing repair darts according to the present invention.

Preferred methods for using single and multi-shot osteochondral flap repair systems according to the present invention are outlined with reference to the schematic of FIG. 19, as follows:

Single Shot:

An osteochondral flap 80 is approximated to the subchondral bone 82 using the single shot guide sleeve 2. The single shot sheath 30 is inserted into the guide sleeve to stabilize the fracture. The single shot trocar 40 is inserted into the sheath. The trocar is used to drill through the osteochondral flap and into bone to form a hole 84 a depth of 20 mm. The trocar 40 is removed, and the 18 mm dart implant 50 is introduced into the rear of the sheath 30. Using the implant pusher 60, the dart implant 50 is installed into the osteochondral flap and subchondrally to fixate the OCD fragment.

Multi Shot

Procedure Using an Implant Gun

The guide sleeve 10 is inserted and the osteochondral flap is compressed. Alternatively, the two-hole guide sleeve 2 can be used, depending on the location and size of the osteochondral flap. A stepped set of drill pins 22 is inserted (either by hand or using a power drill, not shown) to form a set of holes, starting with the shortest pin and ending with the longest pin. The longest pin is removed first and an implant gun 90 (FIG. 20) is used to install the dart 50.

Details of the implant gun are disclosed in previously-referenced U.S. patent application Ser. No. 09/099,869. The barrel 92 of the implant gun is inserted into the guide sleeve to shoot the implant 50 into the osteochondral flap. The process is repeated, remembering to always remove the longest remaining pin.

Before removing the last pin, another pin must be inserted in order to stabilize the guide sleeve. This can be done in two different ways. The first technique is to drill another hole, leaving the pin in until the last implant has been inserted. Alternatively, blunt pin 70 can be inserted into one of the locations where an implant has been inserted. The blunt pin will extend 2 mm into the hole where the implant is.

Manual Implant Insertion Technique

The guide sleeve is inserted and the osteochondral flap is compressed. Again, either the two-hole guide sleeve 2 or the five-hole guide sleeve 10 can be used, depending on the size and location of the osteochondral flap. Selected drill pins are inserted by either hand or power, starting with the shortest pin and ending with the longest pin. Once the holes are formed, the longest pin is removed first and the single shot sheath 30 is inserted into the same hole. The dart 50 is inserted into the back of the sheath. Using the implant pusher, the dart is advanced into the predrilled hole. The steps are repeated for the remaining implants.

Preferred materials for the drill pins, trocar, implant inserter and sheath include stainless steel. The molded handles are ABS plastic. The clear guide sleeves preferably are formed of Plexiglas.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of fixation of osteochondritis dissecans fragments, the method comprising the steps of:
    a) approximating a chondral fragment to bone using a guide sleeve having a plurality of parallel guide tunnels;
    b) inserting a drill through a selected guide tunnel;
    c) drilling a hole through the fragment and into the bone to a predetermined depth;
    d) inserting a fragment-retaining dart into the hole to secure the fragment to the bone; and
    e) repeating steps b)–d) for at least one other selected guide tunnel.

2. The method of claim 1, wherein the implant is inserted in step d) using the guide sleeve as a guide.

3. The method of claim 1, wherein the implant is inserted using a gun.

4. A system for installing osteochondral fragment-retaining darts, comprising:
    a guide sleeve having a plurality of parallel tunnels;
    a trocar sized to be inserted through a selected one of the tunnels for forming a hole in bone; and
    a cannulated dart inserter insertable into the selected one of the tunnels for installing a dart into the hole formed in the bone.

5. The system of claim 4, wherein the trocar comprises a drill pin.

6. The system of claim 4, further comprising a plurality of trocars having various lengths.

7. The system of claim 4, wherein the cannulated dart inserter comprises an implant gun for installing darts.

* * * * *